(12) United States Patent
Ishii

(10) Patent No.: US 9,216,320 B2
(45) Date of Patent: Dec. 22, 2015

(54) METHOD AND APPARATUS FOR MEASURING POWER OUTPUT OF EXERCISE

(71) Applicant: Seiji Ishii, Harwood, TX (US)

(72) Inventor: Seiji Ishii, Harwood, TX (US)

(73) Assignee: Racer Development, Inc., Harwood, TX (US)

( * ) Notice: Subject to any disclaimer, the term of this patent is extended or adjusted under 35 U.S.C. 154(b) by 299 days.

(21) Appl. No.: 13/973,996

(22) Filed: Aug. 22, 2013

(65) Prior Publication Data

US 2015/0057128 A1  Feb. 26, 2015

Related U.S. Application Data

(60) Provisional application No. 61/691,132, filed on Aug. 20, 2012.

(51) Int. Cl.
*A63B 71/00* (2006.01)
*A63B 24/00* (2006.01)

(52) U.S. Cl.
CPC .................................. *A63B 24/0087* (2013.01)

(58) Field of Classification Search
CPC .................................................... A63B 24/0087
See application file for complete search history.

(56) References Cited

U.S. PATENT DOCUMENTS 8,876,738 B1 * 11/2014 Kahn et al. .................... 600/595
8,924,249 B2 * 12/2014 Tropper et al. ............. 705/14.22
8,976,007 B2 * 3/2015 Dugan et al. ................. 340/5.82

* cited by examiner

*Primary Examiner* — Glenn Richman
(74) *Attorney, Agent, or Firm* — Artie Pennington Law Offices, PLLC

(57) ABSTRACT

In a portable exercise tracking system, a method and apparatus for measuring power output of exercise motion by a user. The system includes a wireless motion sensor and a wireless central mass unit. The wireless motion sensor detects, measures and transmits motion data associated with a first motion by the user. The central mass unit detects and measures motion data associated with a second motion by the user. The central mass unit also computes the power output of the first motion and the second motion as a function of the first motion data and the second motion data. The disclosed method and apparatus provides a more effective means of computing total power output of a user performing free body exercises.

13 Claims, 3 Drawing Sheets

METHOD AND APPARATUS FOR MEASURING POWER OUTPUT OF EXERCISE

CROSS-REFERENCE TO RELATED APPLICATIONS

This application claims priority to U.S. Provisional Patent Application Ser. No. 61/691,132 ("Parent Provisional"), filed 22 Aug., 2012. The forgoing Parent Provisional is hereby incorporated by reference in its entirety as if fully set forth herein.

FIELD OF THE INVENTION

This disclosure relates generally to performance monitoring methods and systems, and more specifically to measuring physical, spatial, and physiological parameters and computing total workload.

BACKGROUND OF THE INVENTION

Qualitative analysis of exercise or physical training has historically been based on three parameters: exercise duration, exercise frequency and exercise intensity. Measuring either of the first two parameters is well understood and relatively easy. Measuring the third parameter accurately has historically proven difficult, especially in modes of exercise that involve free body movement.

One method to estimate exercise intensity is through the use of wireless heart rate monitors. A chest strap that measures electrical conduction (EKG) of the heart transmits data to usually a watch type of receiver so that the current heart rate can be viewed during exercise. These have been widely available since the early 1980's and models range from simple monitors that only give current heart rate data to extremely complex monitors that combine GPS data and several data analysis software packages and systems. Although these devices are widely used and have been developed to provide almost every sort of heart rate data available, they are still only estimates of actual work rate during exercise. The heart rate is used as an estimator of the individual's current rate of work output but it is just that, an estimate and not an actual direct measurement of workload being done. The inherent problems of using heart rate to estimate exercise intensity (workload) are that the relationship between heart rate and work rate is not linear, the heart rate response varies between individuals, the heart rate response is affected by environmental factors such as temperature and humidity, the heart rate response is affected but current health status (dehydration, illness, etc.) and an individual's heart rate response varies with changes in fitness levels.

During the early 1980's elite level road cyclists began experimenting with what I believe is the direct measurement of work being done during exercise outside of a laboratory environment. Professionals began testing devices that used strain gauges in the crank to measure torque and with a concurrent angular velocity measurement, an actual power reading could be determined in watts and work being done could be calculated. Commercial versions of these power meters for bicycles became available in the late 1980's, and various models have since been developed. The main difference is where the strain is measured: the crank, the bottom bracket, the rear hub and the pedals are all locations of strain gauges that have been marketed. The advent of the commercially available power meter transformed higher level training; no longer was training volume and intensity being described as time spent in various heart rate zones (with all its inherent shortcomings), training was more accurately described by instantaneous wattage (intensity) and Joules of work (quantity) being done. This created the ability to measure and prescribe actual intensity and actual quantity or work done irrelevant of environmental conditions, change of fitness, equipment being used, etc. Individuals could be compared with absolute numbers and talent identification became much more concrete. Coaching and training became divided with the recreational masses still using heart rate due to the affordability and relatively simpler training analysis and prescriptions while the serious and elite athletes predominantly using direct power (wattage) and work (Joules) to measure, describe and prescribe training.

The development of the bicycle power meter and coaching using this device created markets for software (both web based and computer based) to analyze the data, online coaching services that could now have accurate qualitative and quantitative training data off site and an accurate way to prescribe training, and continued development of competing power measuring devices that created more affordable units. Units measuring things other than mechanical strain are also being developed (they measure the cyclist's opposing forces and combined with known velocity, produce a power measurement).

Compared to heart rate monitors, power meters are still relatively expensive so their market is still small compared to the market for heart rate monitors and their related products and services. Upstream users such as elite athletes, coaches, clinical professions and exercise physiologists understand the need for an actual direct measurement of work for accuracy and have been paying the cost differential since the inception of power meters. The rate at which technology, competition and development have expanded the choices while lowering the entry price in the cycling market points to widespread use in the near future, much like the expansion of heart rate monitors in general fitness.

The methods and apparatus that follow are designed to produce direct measurements of work being done in most exercise situations without the need for work being done on something, as in the bicycle power meter. The bicycle power meter has the advantage of the work is being put into a system that lends itself to measuring force, distance, angular velocity, etc. The measurement of work and power is much more complex with say, weight lifting as the direction of forces being applied, the lack of work being put into a closed system that lends itself to measurements, etc. creates a scenario much more complicated. Fortunately technology is advancing to make actual work measurements such as this and motion tracking and associated motion recognition and motion matching possible with the correct methodology.

Increasing awareness of health benefits derived from physical exercise and participation in athletic events has spawned an increase in the numbers of individuals engaged in these activities. Many individuals train or work out in clubs or indoor gyms using exercise equipment that include various sensors for measuring physical and/or physiological parameters associated with the user's workout. For example, treadmills, elliptical trainers, stair steppers, stationary bicycles, and the like often provide electronic devices that measure or estimate various physical and/or physiological parameters associated with a workout or training exercise, such as the distance traveled, the elapsed time of the exercise, the altitude climbed, the inclination level, the movement rate (e.g., miles per hour, etc.), the heart rate, the power expended, the calories burned, the rate of calories burned, etc. In some gyms or clubs, data relating to an individual's workout may be transmitted automatically from the exercise equipment directly to a computer system and stored. Athletes, their trainers, and/or their coaches may gain access to this data, e.g., for post-workout analysis, to gauge progress or improvement, to develop future workout routines or plans, etc.

Thus a need exists for a method and apparatus that provides a more effective means of computing total power output of a user performing free body exercises.

BRIEF SUMMARY OF THE INVENTION

In accordance with some embodiments, a portable exercise tracking system for measuring the power output of a plurality of motions by a user includes a central mass unit and one or more wireless motion sensors. The central mass unit is placed substantially close to the center of gravity of the user and is adapted to receive mass data which includes a first mass data and a second mass data. The central mass unit also measures a first set of motion data associated with a first detected motion. In addition, the central mass unit is adapted to receive a second set of motion data. The central mass unit calculates a first power output data as a function of the first set of motion data and the first mass data. The central mass unit also calculates a second power output data as a function of the second set of motion data and the second mass data. Finally, the central mass unit calculates a third power output data as a function of the first power output data and the second power output data and transmits the third power output data. The one or more wireless motion sensors are each placed substantially away from the center of gravity of the user. The one or more wireless motion sensors are adapted to measure a second set of motion data associated with the second detected motion. The second detected motion is executed substantially simultaneous with the first detected motion. The one or more wireless motion sensors are also adapted to transmit the second set of motion data.

Figure 1:
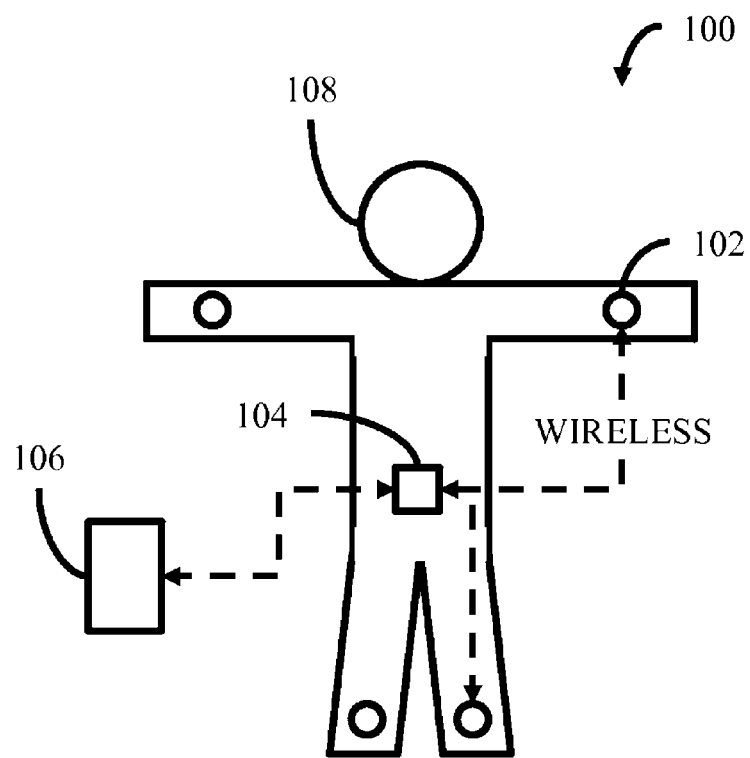
FIG. 1 illustrates in block diagram form, an exercise tracking system according to some embodiments.

In the drawings, similar elements will be similarly numbered whenever possible. However, this practice is simply for convenience of reference and to avoid unnecessary proliferation of numbers, and is not intended to imply or suggest that our invention requires identity in either function or structure in the several embodiments.

DETAILED DESCRIPTION

A. Illustrative Exercise Tracking System

FIG. 1 illustrates in block diagram form a portable exercise tracking system 100 according to some embodiments. The portable exercise tracking system 100 generally includes a plurality of motion sensor 102 placed on the body of the user 108, a central mass unit 104 also placed on the user 108, and a multipurpose electronic device 106. While a plurality of motion sensors 102 are illustrated in FIG. 1, it will be understood that one or more motion sensors 102 can be used depending upon the exercises to be performed and where some sensors measure certain physiological functions in addition to motion. The motion sensor 102 is adapted to communicate wirelessly with the central mass unit 104 by way of a wireless interface. If more than one motion sensor 102 is present in the exercise tracking system 100, all such motion sensors 102 are adapted to communicate wirelessly with the central mass unit 104 by way of a wireless interface. Likewise, the central mass unit 104 is adapted to wirelessly communicate with the plurality of motion sensors 102 by way of a wireless interface. Again, if more than one motion sensor 102 is present in the exercise tracking system 100, all such motion sensors 102 are adapted to wirelessly communicate with the central mass unit 104 by way of a wireless interface. The central mass unit 104 is adapted to wirelessly communicate with the multipurpose electronic device 106 by way of a wireless interface. Likewise, the multipurpose electronic device 106 is adapted to wirelessly communicate with the central mass unit 104 by way of a wireless interface.

B. Illustrative Motion Sensor

Figure 2:
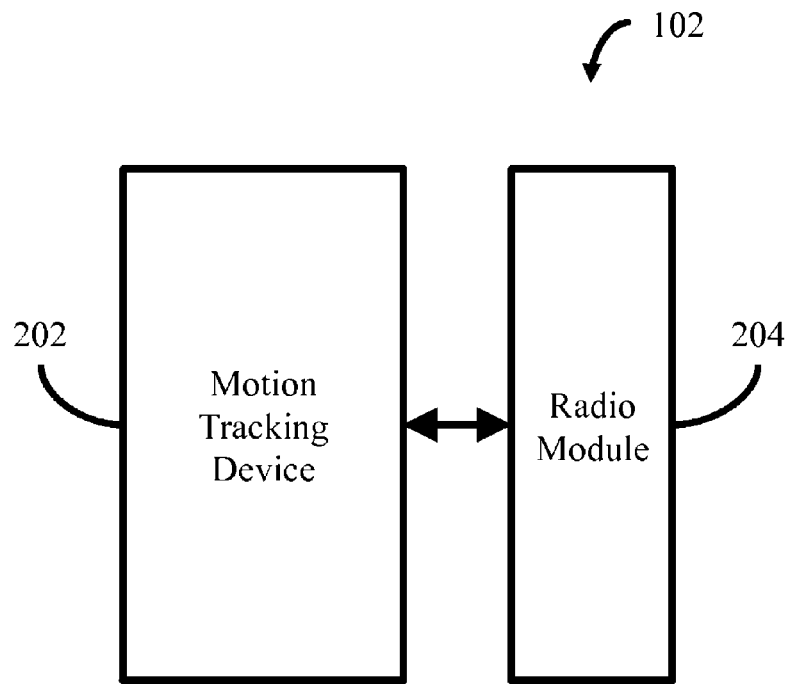
FIG. 2 illustrates in block diagram form, a motion sensor device according to some embodiments.
Figure 3:
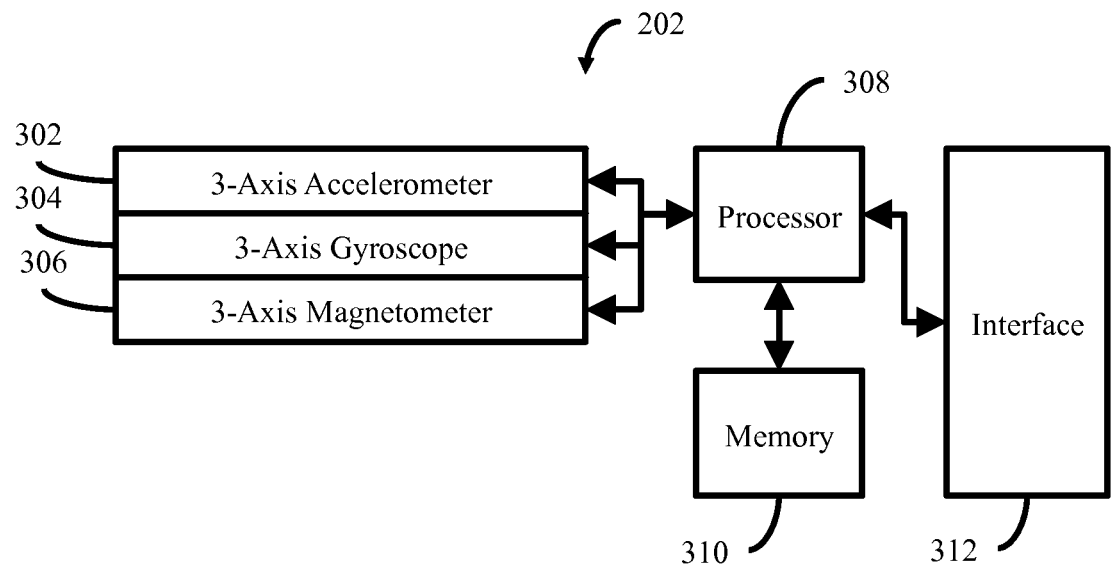
FIG. 3 illustrates in block diagram form, a motion tracking device according to some embodiments.

FIG. 2 illustrates in block diagram form, a motion sensor device 102 according to some embodiments. The motion sensor device 102 generally includes a motion-tracking circuit 202 and a radio circuit 204. FIG. 3 illustrates in block diagram form, a motion tracking device 202 according to some embodiments. The motion-tracking circuit 202 generally includes some or all of the following components: a three-axis accelerometer 302, a three-axis gyroscope 304, a three-axis magnetometer 306, a processor 308, a memory 310 and an interface unit 312. According to some embodiments, the accelerometer, gyroscope, and magnetometer are each Micro-ElectroMechanical Systems ("MEMS") sensors. The processor 308 may comprise a processor, a microprocessor, a microcontroller, a digital signal processor, a math co-processor or other similar processing circuits as well as some combination or subset of the above. The memory 310 may comprise volatile memory, nonvolatile memory or other similar technologies for storing and retrieving stored digital values. The interface unit 312 may comply with industry standard interface standards such as Inter-Integrated Circuit ("I$^2$C"), Synchronous Serial Interface ("SSI") or other similar industry standard interfaces. The motion-tracking circuit 202 and the radio circuit 204 are adapted to communicate with each other by way of industry standard communication interfaces such as I$^2$C, SSI or other similar interfaces. Data output by motion-tracking circuit 202 is digital data. In other embodiments, data output by motion-tracking circuit 202 may be analog in format. The radio circuit 204 is adapted to communicate data wirelessly to an external system by way of industry standard wireless protocols such as Wi-Fi, Bluetooth, Bluetooth LE, ANT, ANT+ or other similar wireless technologies. Radio circuit 204 generally includes an antenna and a receiver/transmitter circuit adapted to wirelessly send and receive information and is generally well known to one of ordinary skill in this art. In certain embodiments, a motion sensor device 102 may be integrated into apparel, such as athletic clothing. For instance, user 108 may wear one or more motion sensor devices 102. Motion sensor device 102 may be incorporated into the clothing of user 108 and/or placed at any desired location of the body of user 108. Different classes of apparel may be utilized in which a given class of apparel has specific sensors configured to be located proximate to a specific portion of the user's 108 body when properly worn. For example, weight lifting apparel may include one or more motion sensor devices 102 positioned on the apparel in a first configuration and yet bicycling apparel may include one or more sensors positioned on apparel in a second configuration.

C. Illustrative Central Mass Unit

Figure 4:
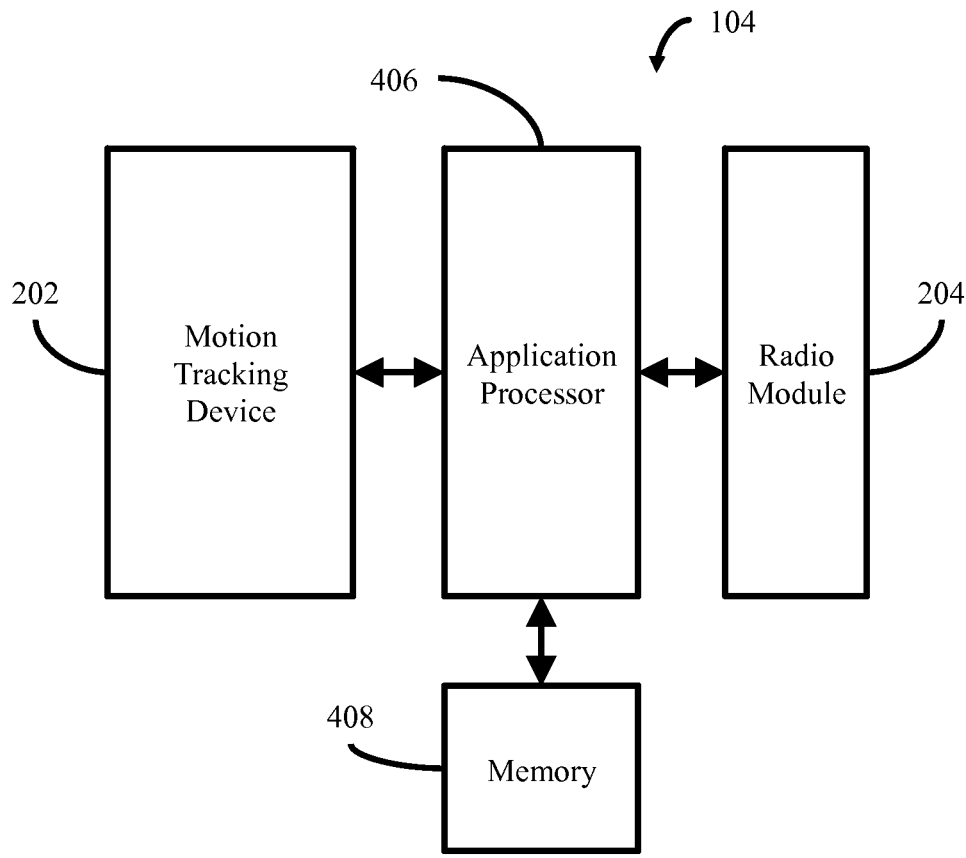
FIG. 4 illustrates in block diagram form, a central mass unit device according to some embodiments.

FIG. 4 illustrates in block diagram form, a central mass unit 104 according to some embodiments. The central mass unit 104 generally includes a motion-tracking circuit 202, an application processor 406, a radio circuit 204, and memory 408. The motion-tracking circuit 202 and the application processor 406 are adapted to communicate with each other by way of industry standard communication interfaces such as I$^2$C, SSI or other similar interfaces. Likewise, application processor 406 and radio circuit 204 are adapted to communicate with each other by way of industry standard communication interfaces such as I$^2$C, SSI or other similar interfaces. Application processor 406 and memory 408 are adapted to communicate with each other by way of industry standard buses that are generally well known to one of ordinary skill in the art. Motion-tracking device 202 is described above and will not be further described here. Likewise, radio module 204 is described above and will not be further described here. Application processor 406 can comprise a processor, a microprocessor, a microcontroller, a digital signal processor, a math co-processor or other similar processing circuits as well as some combination or subset of the above. Memory 408 may include random access memory ("RAM"), read only memory ("ROM"), electronically erasable programmable read only memory ("EEPROM"), flash memory or other memory technology. In certain embodiments, central mass unit 104 may include one or more additional sensors, including but not limited to: a location-determining device (e.g., GPS), temperature sensor (including ambient temperature and/or body temperature), heart rate monitor, image-capturing sensor, moisture sensor and/or combinations thereof. In certain embodiments, central mass unit 104 may be integrated into apparel, such as athletic clothing. Central mass unit 104 includes software or firmware wherein central mass unit 104 is adapted to wirelessly receive data from an external source such as multipurpose electronic device 106. Data received from multipurpose electronic device 106 may include user mass data, mass data associated with an object being moved such as a barbell or dumbbell, or any other mass data needed to compute the power detected and measured by motion sensor 102 and central mass unit 104. In an alternative embodiments, mass data may be detected from a Radio Frequency ID ("RFID") tag embedded or connected to objects such as dumbbells or weights on the barbell. Central mass unit 104 is also adapted to wirelessly receive motion data from motion sensor 102. Data received from motion sensor 102 may include acceleration data, rotational rate data, and magnetic field data or any subset of the above. Central mass unit 104 is also adapted to wirelessly transmit data to multipurpose electronic device 106. Transmitted data from central mass unit 104 may include display data for multipurpose electronic device 106. These data transmissions and receptions are well known to one of ordinary skill in this art.

D. Illustrative Multi-Purpose Electronic Devices

User 108 may possess, carry, and/or wear any number of electronic devices, including multipurpose electronic device 106. In certain embodiments, multipurpose electronic device 106 may not be specially manufactured for fitness or athletic purposes. Indeed, aspects of this disclosure relate to utilizing data from a plurality of devices, some of which are not fitness devices, to collect, detect, and/or measure athletic data. In one embodiment, multipurpose electronic device 106 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage and display device. In one embodiment, multipurpose electronic device 106 may be a computer laptop, a computer tablet, or any other device adapted to wirelessly transmit to or receive data from central mass unit 104. In other embodiments, multipurpose electronic device 106 may be a heart rate monitor display unit, i.e., a watch. Regardless of whether multipurpose electronic device 106 is configured to provide certain output, it may serve as an input device for receiving sensory information and display information from central mass unit 104.

E. Illustrative Operation

Figure 5:
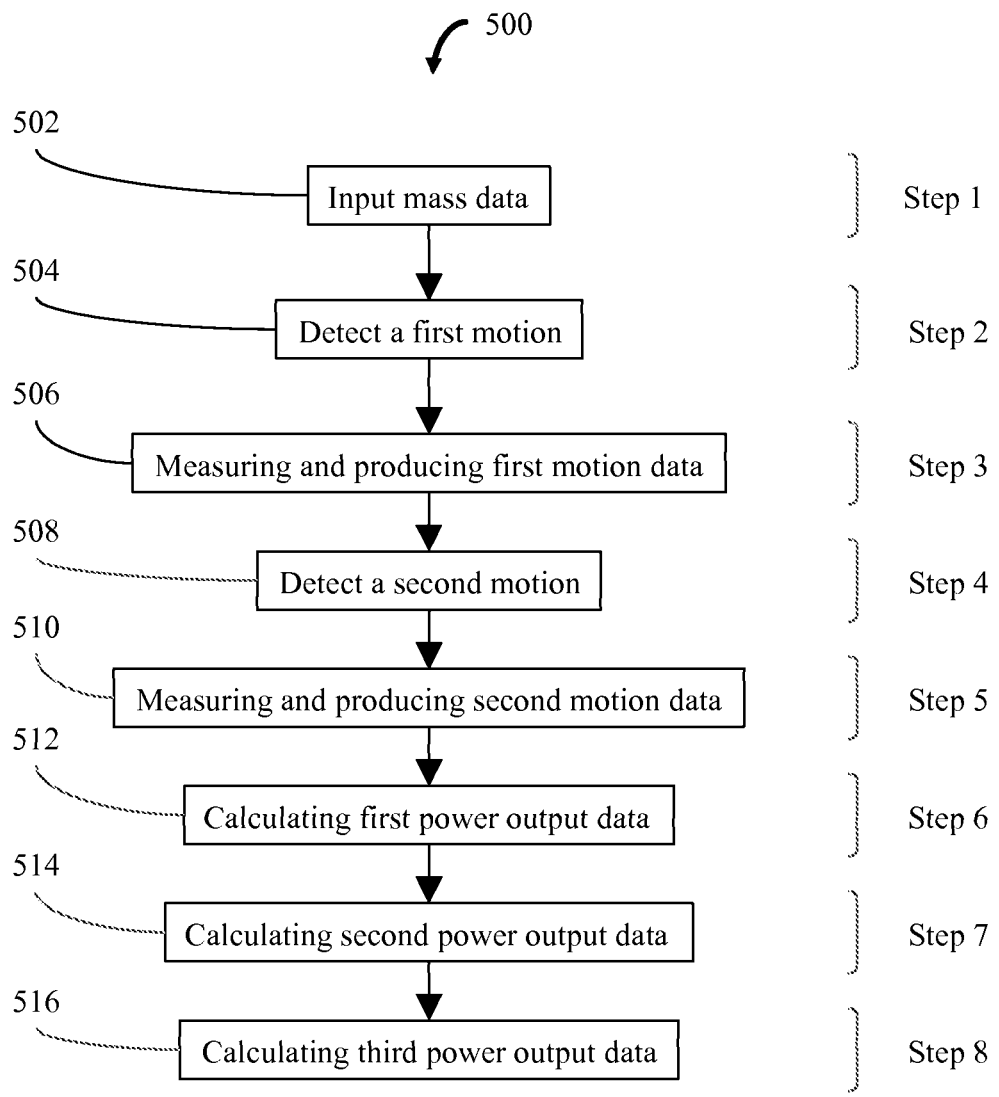
FIG. 5 illustrates in flow chart form, a method for calculating total power according to some embodiments.

FIG. 5 illustrates in flow chart form, a method for calculating total power according to some embodiments. As shown in FIG. 5, the method for calculating total power comprises the following steps:

Step 1: input a first and second mass data.
Step 2: detect a first motion associated with the exercise.
Step 3: measure and produce a first set of motion data.
Step 4: detect a second motion associated with the exercise.
Step 5: measure and produce a second set of motion data.
Step 6: calculate a first power output data based upon the first motion data and the first mass.
Step 7: calculate a second power output data based upon the second motion data and the second mass.
Step 8: calculate a third power output data based upon the first power output data and the second power output data.

An optional ninth step may be added to display the third power output data as a function of time as an example. Other display options may be displaying the third power output data as a final cumulative number, or in any similar function.

Prior to starting the motion sensing and power computation, some mass and biomechanical data is stored on the central mass unit 104 for later processing. Mass data may include the weight and/or mass of user 108, the weight and/or mass of an object or objects being moved by user 108, the height of user 108, and other similar data.

During operation, the central mass unit 104 is placed substantially close to the center of gravity of the user 108, preferably centered at the waist or chest. The motion sensor 102 is placed away from the center of gravity, preferably on the wrist or ankle of user 108. Where additional motion sensors 102 are used, they may be placed on a different wrist or ankle or any other placement where motion may be sensed. User 108 initially maintains a substantially static posture, allowing the central mass unit 104 and, if used, motion sensor 102 to detect a starting point for the exercise motion to be performed as well as allowing an offset to be computed.

User 108 begins exercising performing a series of free body motions, unconstrained by single axis machines such as a Smith machine. Exemplary exercises may include squats, bench presses, dumbbell curls, a clean and jerk, or any similar exercise. Motions detected by the motion sensors 102 and central mass unit 104 will be measured and produced in increments of time related to the sampling frequency. Motion tracking device 202 and central mass unit 104 measure and produce acceleration data using the 3-axis accelerometer, measures and produces rotational rate data using the 3-axis gyroscope, and measures and produces magnetic field data using the 3-axis magnetometer. According to some embodiments, for each time increment, motion sensor produces a set of x, y, and z accelerations data, x, y, and z rotational or angular rate data, and x, y, and z magnetic field data. Exemplary full scale values for x, y, and z acceleration data may range between ±2 g and ±16 g. Exemplary full scale values for x, y, and z rotational rate data may range between ±250°/sec and ±2000°/sec, Exemplary full scale values for x, y, and z magnetic field data may be ±1200 µT. Motion tracking device 202 may output digital data in formats including rotational matrix, quaternion, Euler Angles, or raw data formats.

Algorithms used for calculating power using the motion data are well understood by one of ordinary skill in this art. By way of example, after accumulating the motion data for a particular motion performed during an exercise, the for any particular increment of time where x, y, and z acceleration data has been measured and stored, a first step of deriving the mean of the x, y, or z acceleration data and subtracting the respective mean from the actual x, y, or z acceleration data. Subsequently, a detrend operation is performed to reduce noise in the data set. Detrending removes the mean value from a time-domain signal. The individual velocities of x, y and z are each then calculated by integrating the x, y, and z acceleration data respectively. The distance traveled in the x, y and z direction is subsequently calculated by integrating the x, y, and z velocity data respectively. The distance the user or the object is moved is determined by the taking the square root of the sum of the squares of the respective x, y, and z distance values and subtracting the prior position from the new position. The instantaneous acceleration is determined by taking the square root of the sum of the squares of the respective x, y, and z acceleration value. Work may then be computed as the product of the mass provided, the instantaneous acceleration that is calculated and the distance traveled that is calculated. Power may then be as the computed work divided by the time take to perform the motion.

For complex free body motion, where more than simply the user is moving, each individual sensor may record a set of parallel sequences of motion data which may be then be used to calculate total power output by the user performing the complex motion exercise. Those skilled in the art will recognize computing the total power output by the user performing a bench press is less complex than computing the total power output by the user performing a clean and jerk motion.

Thus it is apparent that we have provided a method and apparatus that provides a more effective means of computing total power output of a user performing free body exercises. Those skilled in the art will recognize that modifications and variations can be made without departing from the spirit of our invention. Therefore, we intend that our invention encompass all such variations and modifications as fall within the scope of the appended claims.

I claim:

1. A portable exercise tracking system for measuring the power output of a plurality of motions by a user comprising:
    a central mass unit placed substantially close to the center of gravity of said user, said central mass unit being adapted to:
        receive a plurality of mass data, said plurality of mass data comprising a first mass data and a second mass data;
        in response to detecting a first motion associated with said plurality of motions by said user, measure a first plurality of motion data associated with said first motion;
        receive a second plurality of motion data;
        calculate a first power output data as a function of said first plurality of motion data and said first mass data;
        calculate a second power output data as a function of said second plurality of motion data and said second mass data;
        calculate a third power output data as a function of said first power output data and said second power output data; and
        transmit said third power output data; and
    a plurality of wireless motion sensors placed substantially away from the center of gravity of said user, said plurality of wireless motion sensors being adapted to:
        in response to detecting a second motion associated with said plurality of motions by said user, said second motion being executed substantially simultaneous with said first motion, measure a second plurality of motion data associated with said second motion; and
        transmit said second plurality of motion data.

2. The portable exercise tracking system of claim 1 wherein said first plurality of motion data further comprises:
    a first acceleration data; a first rotational rate data; and a first magnetic field data.

3. The portable exercise tracking system of claim 2 wherein said central mass unit further comprises a first 3-axis accelerometer, a first 3-axis gyroscope, a first 3-axis magnetometer, a first computational unit, a first memory and a first radio circuit.

4. The portable exercise tracking system of claim 1 wherein said second plurality of motion data further comprises:
    a second acceleration data, a second rotational rate data, and a second magnetic field data.

5. The portable exercise tracking system of claim 4 wherein said central mass unit further comprises a second 3-axis accelerometer, a second 3-axis gyroscope, a second 3-axis magnetometer, a second computational unit, a second memory and a second radio circuit.

6. The portable exercise tracking system of claim 1 further comprising:
    a multi-purpose electronic device adapted to:
        receive said third power output data; and
        display said third power output data.

7. A method for measuring the power output of a plurality of motions by a user comprising:
    inputting a plurality of mass data, said plurality of mass data comprising a first mass data and a second mass data;
    detecting a first motion associated with said plurality of motions by said user;
    measuring and producing a first plurality of motion data associated with said first motion;
    detecting a second motion associated with said plurality of motions by said user, wherein said second motion is executed substantially simultaneous with said first motion;
    measuring and producing a second plurality of motion data associated with said second motion;
    calculating a first power output data as a function of said first plurality of motion data and said first mass data;
    calculating a second power output data as a function of said second plurality of motion data and said second mass data; and calculating a third power output data as a function of said first power output data and said second power output data.

8. The method of claim 7 wherein said first plurality of motion data further comprises:
a first acceleration data; a first rotational rate data; and a first magnetic field data.

9. The method claim 8 wherein said first plurality of motion data is produced by a central mass unit comprising a first 3-axis accelerometer, a first 3-axis gyroscope, a first 3-axis magnetometer, a first computational unit, a first memory, a first battery and a first radio circuit.

10. The method of claim 7 wherein said second plurality of motion data further comprises:
a second acceleration data, a second rotational rate data, and a second magnetic field data.

11. The method of claim 8 wherein said central mass unit further comprises a second 3-axis accelerometer, a second 3-axis gyroscope, a second 3-axis magnetometer, a second computational unit, a second memory, a second battery and a second radio circuit.

12. The method of claim 7 further comprising:
displaying said third power output.

13. A portable exercise tracking system for measuring the power output of a plurality of motions by a user, said portable exercise tracking system comprising:
a central mass unit placed substantially close to the center of gravity of said user, said central mass unit comprising a first 3-axis accelerometer, a first 3-axis gyroscope, a first 3-axis magnetometer, a first computational unit, a first memory and a first radio circuit, said central mass unit being adapted to:
receive a plurality of mass data, said plurality of mass data comprising a first mass data and a second mass data;
in response to detecting a first motion associated with said plurality of motions by said user, measure a first plurality of motion data associated with said first motion, said first plurality of motion data comprising a first acceleration data; a first rotational rate data; and a first magnetic field data;
receive a second plurality of motion data;
calculate a first power output data as a function of said first plurality of motion data and said first mass data;
calculate a second power output data as a function of said second plurality of motion data and said second mass data;
calculate a third power output data as a function of said first power output data and said second power output data; and
transmit said third power output data;
a plurality of wireless motion sensors placed substantially away from the center of gravity of said user, each of said plurality of wireless motion sensors comprising a second 3-axis accelerometer, a second 3-axis gyroscope, a second 3-axis magnetometer, a second computational unit, a second memory and a second radio circuit being adapted to:
in response to detecting a second motion associated with said plurality of motions by said user, said second motion being executed substantially simultaneous with said first motion, measure a second plurality of motion data associated with said second motion; said second plurality of motion data comprising a second acceleration data; a second rotational rate data; and a second magnetic field data; and
transmit said second plurality of motion data;
a multi-purpose electronic device adapted to:
receive said third power output data; and
display said third power output data.

* * * * *